United States Patent
Pei et al.

(10) Patent No.: US 9,638,772 B2
(45) Date of Patent: May 2, 2017

(54) CONNECTOR AND MEDICAL EQUIPMENT

(71) Applicants: Jian Hua Pei, Shenzhen (CN); Ting Qiang Xue, Shenzhen (CN); Wen Qiang You, Shenzhen (CN)

(72) Inventors: Jian Hua Pei, Shenzhen (CN); Ting Qiang Xue, Shenzhen (CN); Wen Qiang You, Shenzhen (CN)

(73) Assignee: Siemens Aktiengesellschaft, München (DE)

( * ) Notice: Subject to any disclaimer, the term of this patent is extended or adjusted under 35 U.S.C. 154(b) by 619 days.

(21) Appl. No.: 14/083,435

(22) Filed: Nov. 18, 2013

(65) Prior Publication Data

US 2014/0139222 A1 May 22, 2014

(30) Foreign Application Priority Data

Nov. 19, 2012 (CN) .......................... 2012 1 0468044

(51) Int. Cl.
*G01V 3/00* (2006.01)
*G01R 33/38* (2006.01)
*A61B 5/055* (2006.01)

(52) U.S. Cl.
CPC .......... *G01R 33/3802* (2013.01); *A61B 5/055* (2013.01); *A61B 2560/0443* (2013.01); *A61B 2562/225* (2013.01); *Y10T 403/32631* (2015.01)

(58) Field of Classification Search
CPC .... G01R 33/3802; G01R 33/44; A61B 5/055; A61B 2560/0443; A61B 2562/225; F16C 11/06; Y10T 403/3263
USPC ........................... 324/322; 403/122; 312/209
See application file for complete search history.

(56) References Cited

U.S. PATENT DOCUMENTS

| | | | | |
|---|---|---|---|---|
| 4,808,957 A * | 2/1989 | Furukawa | ............ | G01R 33/421 324/318 |
| 5,274,332 A * | 12/1993 | Jaskolski | ......... | G01R 33/34007 324/318 |
| 6,313,632 B1 * | 11/2001 | Aoki | .................... | G01R 33/383 324/318 |
| 6,717,408 B2 * | 4/2004 | Minas | ................ | G01R 33/3806 324/307 |
| 8,118,488 B2 * | 2/2012 | Gregerson | ........... | A61B 5/0555 378/196 |
| 2004/0162480 A1 * | 8/2004 | Satragno | .............. | A61B 5/0555 600/415 |
| 2006/0006866 A1 * | 1/2006 | Roozen | ............. | G01R 33/3854 324/318 |
| 2006/0238598 A1 * | 10/2006 | Jung | .................... | G03G 15/326 347/138 |

(Continued)

FOREIGN PATENT DOCUMENTS

GB        2472794 A  *  2/2011  ............ A61B 6/035
JP        63128610 A  *  6/1988

*Primary Examiner* — Susan Lee
(74) *Attorney, Agent, or Firm* — Lempia Summerfield Katz LLC

(57) ABSTRACT

A connector and medical equipment are provided. The connector includes at least one framework and at least one fastening structure. The at least one connector is used to connect a main body and a housing. The at least one framework is arranged along the outside of the main body. The fastening structure is located on the at least one framework. The at least one fastening structure is used to connect the housing.

15 Claims, 4 Drawing Sheets

(56) References Cited

U.S. PATENT DOCUMENTS

| | | | | |
|---|---|---|---|---|
| 2011/0192434 A1* | 8/2011 | Young | ............... | A45B 11/00 |
| | | | | 135/20.1 |
| 2011/0238768 A1* | 9/2011 | Habets | ............... | G06F 11/0748 |
| | | | | 709/206 |
| 2012/0048316 A1* | 3/2012 | Fournillier | ............... | A45B 11/00 |
| | | | | 135/16 |

* cited by examiner

CONNECTOR AND MEDICAL EQUIPMENT

This application claims the benefit of CN 201210468044.8, filed on Nov. 19, 2012, which is hereby incorporated by reference in its entirety.

TECHNICAL FIELD

The present embodiments relate to a connector for connecting a housing and a main body of medical equipment.

BACKGROUND

Magnetic resonance imaging is a bio-magnetic nuclear spin imaging technology developed rapidly along with the development of computer technology, electronic circuit technology, and superconductor technology. In magnetic resonance imaging, human tissue is placed in a static magnetic field $B_0$, and hydrogen nuclei within the human tissue are excited by a radio-frequency pulse with the same frequency as a precession frequency of the hydrogen nuclei, so as to cause resonance of the hydrogen nuclei and absorb energy. After the radio-frequency pulse is stopped, the hydrogen nuclei send out a radio signal at a specific frequency and release the absorbed energy. The energy is received by a receiver in vitro and is processed by a computer to obtain an image.

In a typical magnetic resonance imaging system, the magnetic field is generated by a superconducting magnet. The superconducting magnet and an auxiliary device related to the magnet and used as the main body of the magnetic resonance imaging system may be wrapped in a housing. The purposes of the housing are aesthetic and for protecting the main body and reducing noise. The housing and the main body are to be connected by a corresponding connector. The connector has a complex structure in the prior art, so the installation and detachment of the connector is time-consuming. It is easy to damage the main body or the housing during installing or detaching. In addition, since the structure of the connector is complex, the manufacturing cost of the connector in the prior art is comparatively high.

SUMMARY AND DESCRIPTION

In order to simplify the installation of the housing of a magnetic resonance imaging system, a connector that is used to connect a main body and a housing is provided. The connector includes a framework and a fastening structure. The framework is arranged along the outside of the main body. The fastening structure is located on the framework, and the fastening structure is used to connect the housing.

In one embodiment, the framework includes a chute, and the fastening structure may move on the chute.

In one embodiment, medical equipment including a main body, a housing and a connector is provided.

In one embodiment, the medical equipment is a magnetic resonance imaging system, and the main body is a magnet. In another embodiment, the medical equipment is a computed tomography scanner, and the main body is a rack.

The medical equipment according to one or more the present embodiments (e.g., the magnetic resonance imaging system) is easy to install and cheap to manufacture.

DETAILED DESCRIPTION

A connector includes at least one framework (e.g., a framework) and at least one fastening structure (e.g., a fastening structure). The connector is used to connect a main body and a housing. The framework is arranged along the outside of the main body. The fastening structure is located on the framework. The fastening structure is used to connect the housing.

Figure 1:
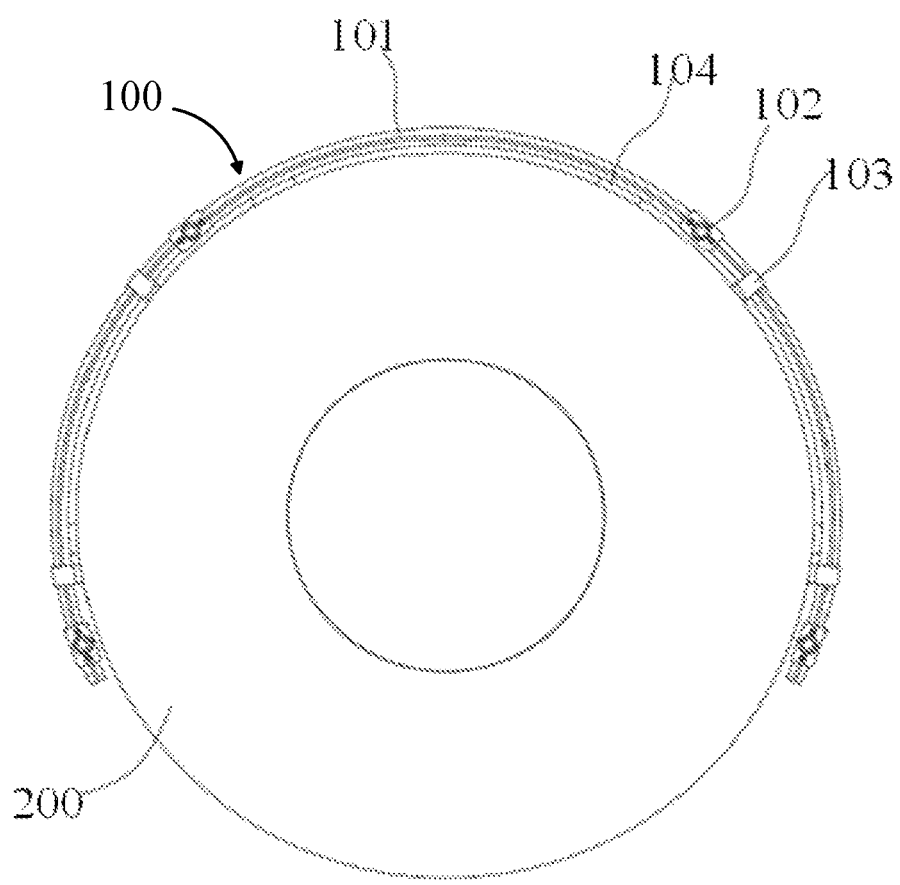
FIG. 1 is a front view of a main body of medical equipment and a connector according to one embodiment.
Figure 2:
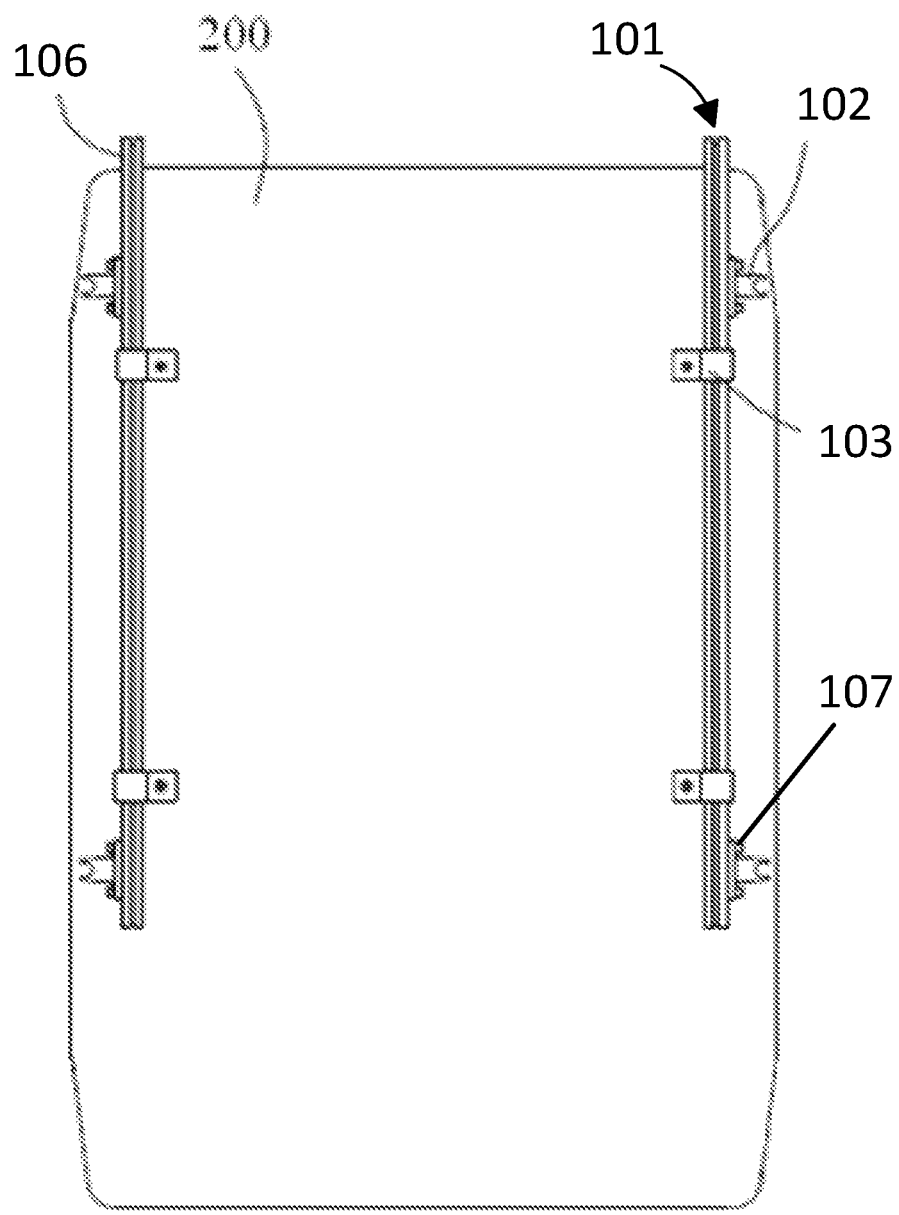
FIG. 2 is a side view of a main body of medical equipment and a connector according to one embodiment.
Figure 3:
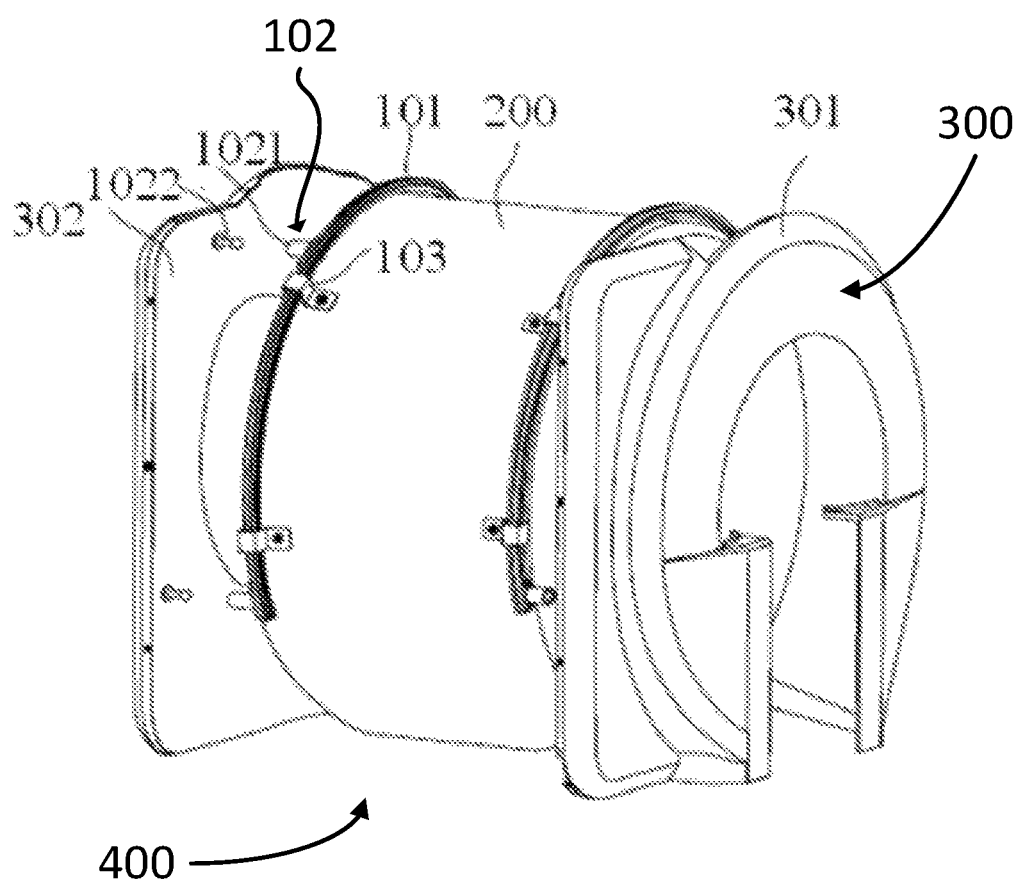
FIG. 3 is a stereogram of a main body and a housing of medical equipment and a connector according to one embodiment.

FIG. 1 is a front view of a main body of medical equipment and a connector according to one embodiment. FIG. 2 is a side view of a main body of medical equipment and a connector according to one embodiment. FIG. 3 is a stereogram of a main body and a housing of medical equipment and a connector according to an embodiment.

As shown in FIG. 1, one embodiment of a connector 100 includes a framework 101 and a fastening structure 102. The connector 100 is used to connect a main body 200 and a housing of medical equipment. The framework 101 is arranged along the outside of the main body 200. The fastening structure 102 is located on the framework 101. The fastening structure 102 is used to connect the housing 300.

As shown in FIG. 1, the framework 101 forms three quarters of a ring along a periphery of the main body 200, and is detachably installed on the main body 200 using at least one cradle 103 (e.g., a cradle). The framework 101 may be made of different kinds of non-magnetic material, such as aluminum and stainless steel profiles and the like. A shock absorption structure (e.g., a shock absorption structure 104 made of a layer of a damping material used to reduce noise) is arranged between the framework 101 and the main body 200. The use of the fastening structure 102 reduces the number of cradles 103 in the prior art, and the performance of the fastening structure 102 is more stable and may provide higher installation precision.

As shown in FIG. 2, the framework 101 includes a chute (e.g., chute 106). The fastening structure 102 has a structure that matches the chute and is thus able to move on the chute. The fastening structure 102 includes a ball-socket joint that is installed on the framework 101, and the fastening structure 102 may move in the chute of the framework 101, so the position of the fastening structure 102 on the framework 101 may be adjusted. A bottom of the ball-socket joint of fastening structure 102 is installed on a locating structure (e.g., locating structure 107, as shown in FIG. 2) of the fastening structure 102 that matches the ball-socket joint. The locating structure has a redundant space that is perpendicular to the direction of the chute, so the ball-socket joint of the fastening structure may also move slightly in the direction perpendicular to the chute. The locating structure may be a mechanical structure, such as a screw, a buckle, a pin or the like.

As shown in FIG. 3, the housing 300 of medical equipment 400 includes a front cover 301 and a rear cover 302. The front cover 301 and the rear cover 302 are respectively installed on a front face and a rear face of the main body 200. The front cover 301 and the rear cover 302, respectively, have a ball-shaped joint 1022 corresponding to a ball-socket joint 1021 of the fastening structure 102. The front cover 301 and the rear cover 302 are installed on the fastening structure 102 using the ball-shaped joints 1022 and the ball-socket joints 1021. The matching between the ball-socket joints 1021 of the fastening structure 102 and the ball-shaped joints 1022 of the front cover 301 and the rear cover 302 provides easy operability and high efficiency. In addition, since the fastening structure 102 is adjustably installed on the framework 101, the effect of creating tolerances may be effectively excluded (e.g., the matching of relative positions of the ball-socket joints 1021 of the at least one fastening structure 102 and the ball-shaped joints 1022 of the front cover 301 and the rear cover 302), and higher installation precision may thus be achieved.

Figure 4:
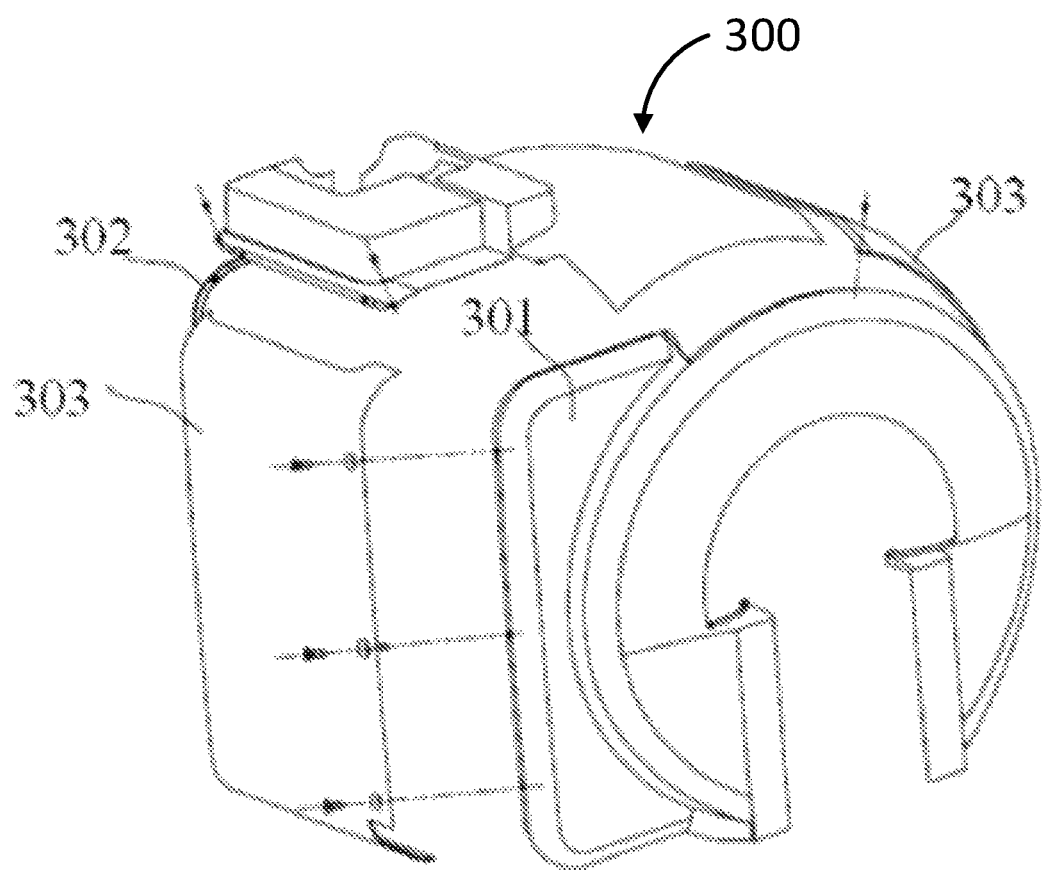
FIG. 4 is a stereogram of a housing of medical equipment according to one embodiment.

FIG. 4 is a stereogram of a housing of medical equipment according to one embodiment, and as shown in FIG. 4, the housing also includes side covers 303. The side covers 303 are directly installed on the front cover 301 and the rear cover 302, for example, using screws, pins or ball-socket joints. The side covers 303 are directly installed on the front cover 301 and the rear cover 302, avoiding redundant installation parts, simplifying the installation structure, providing higher installation precision, and providing an attractive appearance.

The medical equipment according to an embodiment may be a magnetic resonance imaging system. In such a case, the main body 200 is a magnet. In another embodiment, the medical equipment may be a computed tomography scanner. In such a case, the main body 200 is a support.

In one embodiment, a connector and medical equipment are provided. The connector includes at least one framework (e.g., a framework) and at least one fastening structure (e.g., a fastening structure). The connector is used to connect a main body and a housing. The framework is arranged along the outside of the main body. The fastening structure is located on the framework. The fastening structure is used to connect the housing. The performance of the connector of one or more of the present embodiments is more stable and may provide higher installation precision. Redundant installation parts are avoided, the installation structure is simplified, the price is low, and an attractive appearance is provided.

The above describes embodiments of the invention and does not limit the invention. Any modification, equivalent replacement, improvement, etc. made within the spirit and principle of the invention is included in the protective scope.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A connector for connecting a main body and a housing of medical equipment, wherein the housing comprises at least one ball-shaped joint, and wherein the medical equipment is a magnetic resonance imaging system and the main body is a magnet, or the medical equipment is a computed tomography scanner and the main body is a rack, the connector comprising:
   a framework; and
   a fastening structure, wherein the fastening structure comprises at least one ball-socket joint,
   wherein the at least one ball-socket joint corresponds to the at least one ball-shaped joint one by one and matches the at least one ball-shaped joint,
   wherein the framework is arranged along the outside of the main body, and
   wherein the fastening structure is located on the framework, and the fastening structure is usable to connect the housing and the main body.

2. The connector of claim 1, wherein the framework comprises a chute, and the fastening structure is moveable on the chute.

3. The connector of claim 1, further comprising a locating structure, the locating structure being usable to fix the fastening structure to the framework.

4. The connector of claim 1, further comprising a shock absorption structure, the shock absorption structure being located between the framework and a magnet.

5. The connector of claim 4, wherein the shock absorption structure is a gasket or a support.

6. The connector of claim 1, wherein the fastening structure is a ball-socket joint.

7. The connector of claim 2, further comprising a locating structure, the locating structure being usable to fix the fastening structure to the framework.

8. Medical equipment comprising:
   a main body;
   a housing, wherein the housing comprises at least one ball-shaped joint; and
   a connector for connecting the main body and the housing, the connector comprising:
      a framework; and
      a fastening structure, wherein the fastening structure comprises at least one ball-socket joint,
   wherein the at least one ball-socket joint corresponds to the at least one ball-shaped joint one by one and matches the at least one ball-shaped joint,
   wherein the framework is arranged along the outside of the main body,
   wherein the fastening structure is located on the framework, and the fastening structure is usable to connect the housing and the main body, and
   wherein the medical equipment is a magnetic resonance imaging system, and the main body is a magnet, or wherein the medical equipment is a computed tomography scanner, and the main body is a rack.

9. The medical equipment of claim 8, wherein the housing comprises a front cover, a rear cover and at least one side cover, and
   wherein the front cover and the rear cover are connected to the connector, and the side cover is connected to the front cover and the rear cover.

10. The medical equipment of claim 8, wherein the framework comprises a chute, and the fastening structure is moveable on the chute.

11. The medical equipment of claim 8, wherein the connector further comprises a locating structure, the locating structure being usable to fix the fastening structure to the framework.

12. The medical equipment of claim 8, wherein the connector further comprises a shock absorption structure, the shock absorption structure being located between the framework and a magnet.

13. The medical equipment of claim 12, wherein the shock absorption structure is a gasket or a support.

14. The medical equipment of claim 8, wherein the fastening structure is a ball-socket joint.

15. The connector of claim 10, wherein the connector further comprises a locating structure, the locating structure being usable to fix the fastening structure to the framework.

* * * * *